United States Patent [19]

Warrin

[11] Patent Number: 4,487,582
[45] Date of Patent: Dec. 11, 1984

[54] DENTAL CLEANING SYSTEM

[75] Inventor: George E. Warrin, North Merrick, N.Y.

[73] Assignee: Cooper LaserSonics, Inc., Santa Clara, Calif.

[21] Appl. No.: 467,816

[22] Filed: Feb. 18, 1983

[51] Int. Cl.³ .............................................. A61C 3/02
[52] U.S. Cl. ...................... 433/88; 51/436; 51/438; 55/523; 137/550; 251/5
[58] Field of Search ............... 433/88, 125, 216; 51/426, 427, 428, 436, 437, 438, 439; 251/4, 5, 7, 8, 358; 137/550; 222/630, 173; 118/308; 55/523

[56] References Cited

U.S. PATENT DOCUMENTS

| 2,236,477 | 3/1941 | Fuchs | 137/550 |
|---|---|---|---|
| 2,409,768 | 10/1946 | Lavett et al. | 251/5 |
| 2,576,008 | 11/1951 | Gladfelter et al. | 51/427 |
| 2,604,958 | 7/1952 | Leufrenius | 55/523 |
| 2,661,537 | 12/1953 | Angell | 433/88 |
| 2,665,035 | 1/1954 | Schemm | 51/438 |
| 2,804,168 | 8/1957 | Church | 55/523 |
| 2,896,663 | 7/1959 | Mena | 137/550 |
| 3,155,110 | 11/1964 | Hoffman | 137/550 |
| 3,350,053 | 10/1967 | Schmitz | 251/7 |
| 3,415,276 | 12/1968 | Lind et al. | 251/7 |
| 3,527,027 | 9/1970 | Knight et al. | 55/523 |
| 3,557,536 | 1/1971 | Ririe | 55/523 |
| 3,835,884 | 9/1974 | Ishikawa et al. | 137/550 |
| 3,882,638 | 5/1975 | Black | 51/428 |
| 3,972,123 | 8/1976 | Black | 433/88 |
| 4,174,571 | 11/1979 | Gallant | 51/428 |
| 4,214,871 | 7/1980 | Arnold | 433/88 |

Primary Examiner—John J. Wilson
Attorney, Agent, or Firm—Thomas R. Boland

[57] ABSTRACT

Soluble abrasive cleaning powder fed from a fluid-tight chamber and entrained in a stream of air is directed against a tooth surface to be cleaned from a manually controlled handpiece. The handpiece includes an improved air supply and control system having a first conduit for supplying air under pressure to the handpiece, a second conduit connected to the first for supplying air under pressure into the bottom portion of the fluid-tight chamber for entraining cleaning powder to be discharged through an outlet opening in the fluid-tight chamber and a third conduit connected to the first and to the fluid-tight chamber for directing a flow of air into the chamber at a point above the level of the cleaning powder in the chamber. A flow restricter and air filter are connected in the third conduit with the air filter being located in the fluid-tight chamber for filtering air flowing into and out of the system through the third conduit.

16 Claims, 4 Drawing Figures

DENTAL CLEANING SYSTEM

BACKGROUND OF THE INVENTION

1. Field of the Invention

This invention relates to apparatus for cleaning teeth, and more particularly to an improved dental cleaning system for removal of tenacious stain and heavy plaque from exposed tooth surfaces by simultaneously directing a stream of air containing entrained cleaning powder and a stream of water onto the surface to be cleaned.

2. Description of the Prior Art

While an effective home care program including regular brushing and flossing is considered essential to dental hygiene, such home care normally cannot be completely effective in removing stain and plaque particularly from relatively inaccessible surfaces between the teeth and from pits and fissures. Accordingly, it is normally recommended that a dental care program include periodic professional cleaning. Such professional cleaning conventionally has involved the removal of calculus, particularly from subgingival surfaces, and the cleaning of exposed enamel surfaces for the removal of stain and plaque by polishing the enamel surface with a rubber cup and an abrasive material, typically pumice, in a paste. This method is effective in cleaning accessible surfaces, but cannot remove all stains from deep pits and fissures.

It has also been known, for example from U.S. Pat. Nos. 3,882,638 and 3,972,123, to employ air abrasive equipment for cleaning teeth, using insoluble abrasive particles entrained in an air stream directed onto the tooth surface while simultaneously discharging a water stream onto the surface. Soluble abrasive cleaning particles or pellets, and powdered abrasive cleaning material, respectively, are disclosed in U.S. Pat. Nos. 4,214,871 and 4,174,571.

The prior art abrasive cleaning devices which have been most widely used commercially employ water delivered in one or more streams adjacent to or surrounding the air abrasive stream to provide a wet surface for more effective cleaning, to eliminate dust from within the patient's mouth, and to dissolve and flush abrasive material from the tooth surface for removal by conventional suction equipment. Although insoluble abrasives have met with only limited acceptance, soluble abrasive material is widely used for professional cleaning of teeth. In particular, sodium bicarbonate abrasive cleaning powder (hereinafter cleaning powder) has been widely accepted and is very effective in removing stain and plaque even from deep pits and fissures.

Difficulty has been encountered in reliably delivering both soluble and insoluble cleaning abrasive materials at a uniform, accurately controllable rate. Dispensing and conveying solid cleaning materials through complex conduit and valving systems by pressurized air has presented difficulty, particularly since it has generally been necessary to vary air pressure and/or flow rate in order to control and vary the amount of abrasive cleaning material delivered to the handpiece. Filters used in the air system generally have been of the disposable type which could not be serviced or cleaned and which if not changed at proper intervals, could result in further difficulty in controlling flow rates and pressures. Similarly, pinch valves used to stop flow through flexible tubing of the system have not always been reliable and have presented substantial difficulty in operation.

The prior art systems of this general type generally have included a separate, valve controlled bleed-off system for depressurizing the cleaning powder supply and dispensing apparatus and the pressurized powder dispensing conduit upon shut-down of the system. Such bleed-off systems required separate filter mechanism for removing and collecting cleaning powder bled from the system to prevent it from being discharged into the open atmosphere. Such filtered bleed-off systems also presented additional service requirements, and sudden bleed-off of air from the pressurized supply container could result in substantial volumes of cleaning material being carried away and wasted.

SUMMARY OF THE INVENTION

It is the primary object of the present invention to provide an improved air abrasive dental cleaning system of the type employing a soluble cleaning powder entrained in and delivered by a stream of air onto the surface to be cleaned while simultaneously discharging a stream of water onto the surface to be cleaned.

Another object is to provide such system which includes an improved more reliable system for supplying cleaning powder to the air abrasive outlet in the handpiece of the cleaning apparatus.

Another object is to provide such an improved system which is more reliable in operation and which can be easily and quickly serviced by relatively unskilled personnel to maintain a reliable, accurately controlled rate of dispensing cleaning powder.

Another object is to provide an improved, easily servicable, extended use filter for use in such a cleaning powder supply system.

Another object of the invention is to provide an improved cleaning powder supply system having an improved flow control valve for controlling the flow of cleaning powder and air through the system.

In the attainment of the foregoing and other objects and advantages, an important feature resides in providing an efficient pressurized air delivery and control system for maintaining a highly uniform flow of air for dispensing and conveying cleaning powder from a supply thereof, including an improved valve and filter system which effectively maintains the flow of cleaning powder to the handpiece used in cleaning the teeth while effectively preventing the escape of cleaning powder into any portion of the system other than the line leading from the cleaning powder supply to the handpiece outlet nozzle. Improved filters which may readily and easily be manually disassembled and cleaned, and which incorporate means for preventing reverse flow through the filter element are included in the system, and an improved bleed-off filter mounted within the cleaning powder supply chamber is connected in a bleed line containing flow restriction means for bleeding pressure from the supply chamber upon shut-down of the system without permitting the escape of cleaning powder into the bleed system. An improved air-actuated pinch valve mechanism is provided to more positively cut off flow of air and entrained cleaning powder from the supply system upon actuation of the control switch to the valve.

BRIEF DESCRIPTION OF THE DRAWINGS

Other features and advantages of the invention will become apparent from the detailed description contained hereinbelow, taken in conjunction with the drawings, in which.

DETAILED DESCRIPTION OF THE PREFERRED EMBODIMENTS

Figure 1:
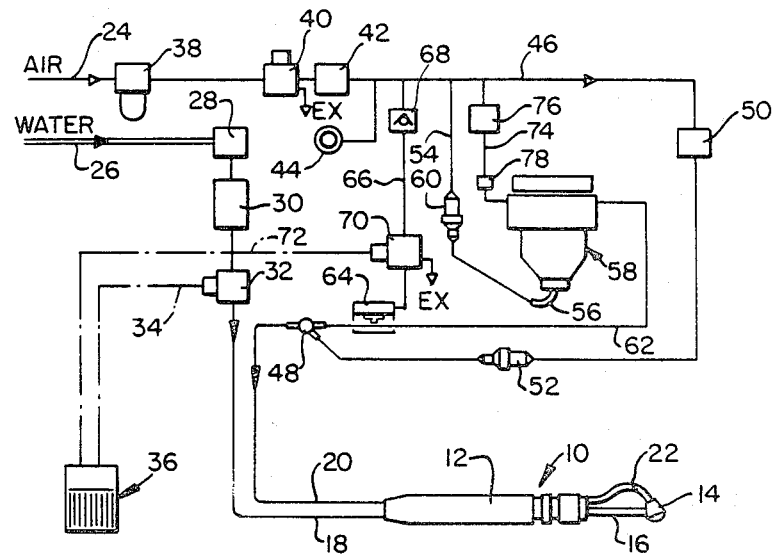
FIG. 1 is a schematic illustration of a dental cleaning system according to the present invention.

Referring now to the drawings in detail, a handpiece used in directing an air-abrasive stream and surrounding water spray curtain onto the surface of teeth to be cleaned is designated generally by the reference numeral 10 and includes an elongated handle portion 12 and a nozzle head 14 supported on a rigid water supply tube 16. A flexible water supply conduit 18 extends into the handle 12 and is connected to the rigid tube 16 within the handpiece for supplying water under pressure to the head 14. A second flexible supply conduit 20 also extends into the handle 12 and is connected to a removable, flexible tube 22 for supplying air under pressure and entrained cleaning powder to the cleaning head 14. Air is supplied to the apparatus through an air supply line 24 from a suitable compressed air source such as a conventional dental office air supply compressor, not shown, and water is supplied through a separate line 26 from a suitable source such as a municipal water supply line. A water pressure regulator 28 is connected in line 26 to adjust the water pressure at a constant desired level, and a suitable heater 30 connected in the water supply line maintains the water to the handpiece at a desired temperature which will be comfortable to a patient. Flow of warm water to the handpiece is controlled by a solenoid actuated valve 32 connected, through line 34, to a three-position foot actuated control switch 36. The water supply system and the structure of the handpiece, per se, may be of conventional construction and as such form no part of the present invention other than being necessary to the overall operation of the dental cleaning system.

Referring still to the schematic of FIG. 1, air under pressure flowing through line 24 passes initially through an inlet, or preliminary filter 38 which removes water, contaminates, dust particles and the like, then through a main solenoid actuated shut-off valve 40 and pressure reducer-regulator 42 which maintains the air pressure to the apparatus at a constant, desired level. A suitable gauge 44 may be provided downstream of regulator 42 to provide a continuous visible display of system air pressure. Valve 40 is vented to atmosphere to bleed pressure from the system, through line 46, when the valve is closed. From pressure regulator valve 42, air flows through line 46 and a suitable variable flow restrictor, preferably a manually operated needle valve 50. An improved air filter and one-way check valve 52 is also connected in line 46 to further filter the air flowing to the handpiece 10 and to prevent reverse flow through the filter. Air flows through air filter and one-way check valve 52 to a Y-fitting 48 connected to the flexible air conduit 20 to supply air to the handpiece 10.

Air also flows from line 46 through line 54 to the coupling member 56 mounted on the bottom of a powder chamber assembly designated generally as 58. A second combined air filter and check valve 60 is connected in line 54. From chamber 58 air flows through a line 62 to the Y-fitting 48 to deliver entrained cleaning powder particles to the flexible conduit 20 to flow with air from line 46 through handpiece 10 and flexible tube 22 to be discharged from the cleaning head 14. Flow of air and cleaning powder particles through line 62 is controlled by a normally closed air energized diaphragm actuated pinch valve 64. Actuating air is supplied to valve 64 through a line 66 connected to line 46, and a one-way check valve 68 connected in line 66 prevents reverse flow through this line.

Flow through line 66 to valve 64 is controlled by a three way normally open, energized closed solenoid valve 70 connected, through line 72 to the foot actuated control switch 36. When valve 70 is energized, pinch valve 64 is vented to atmosphere to permit the pinch valve to open and air to flow through line 62.

When pinch valve 64 is energized to close line 62, cleaning powder chamber 58 will normally remain pressurized through line 54 and through a second conduit 74 connected between line 46 and an inlet in the top portion of chamber 58. As indicated schematically in FIG. 1 and described more fully hereinbelow, a flow restrictor 76 connected in line 74 limits the rate of flow through this line and an air filter 78 connected in the line serves both to filter air flowing into chamber 58 and to prevent cleaning powder particles from escaping into the system when the system is vented to atmosphere by closing main flow control valve 40. With valve 40 closed and the system vented to atmosphere through this valve, chamber 58 can be opened for cleaning and servicing or for refilling with cleaning powder as soon as gauge 44 indicates system pressure has reached zero. With valve 40 open normal bleed air flows through line 46 and tube 20 to be discharged from handpiece 10. With valve 40 open and control switch 36 actuated to its first detent position, water flow control valve is energized open to permit flow of irrigation or rinsing water through handpiece 10. When the foot actuated control 36 is moved to its second detent or fully depressed position, water control valve 32 will remain open, and valve 70 will be energized to depressurize and release pinch valve 64 to permit a flow of particulate cleaning powder and air from chamber 58 through line 62 to handpiece 10.

Figure 2:
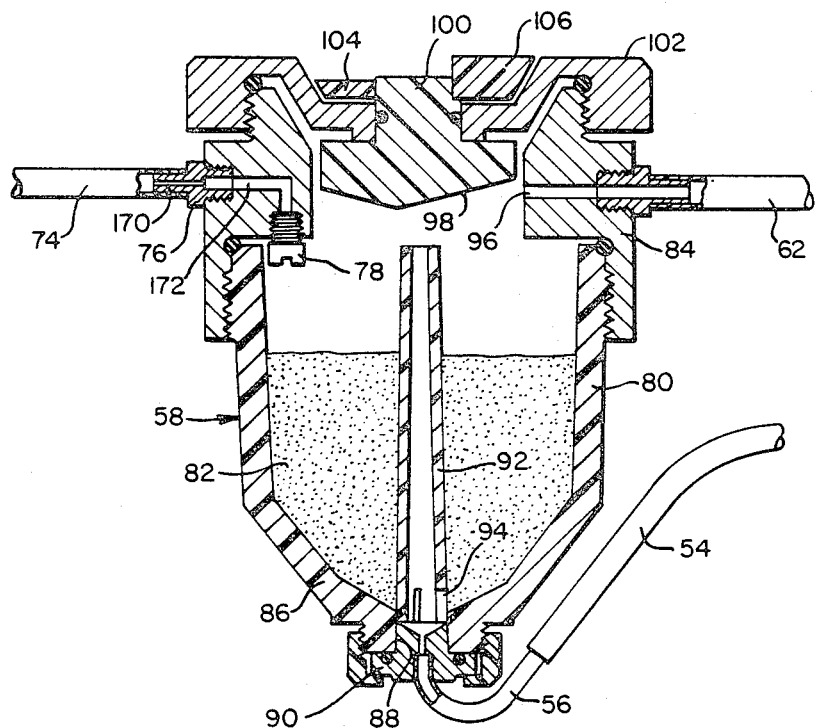
FIG. 2 is an enlarged sectional view of a dental powder supply and dispensing mechanism suitable for use in the cleaning system of the present invention.

An improved cleaning powder supply chamber and dispensing mechanism 58 suitable for use in combination with the present invention is illustrated in FIG. 2. Except for the flow restrictor 76 and filter 78 in line 74, the structure illustrated in FIG. 2 is not a part of the present invention, but is the subject of a separate patent application assigned to the assignee of the present invention and filed concurrently herewith.

The supply chamber 58 includes a cleaning powder hopper, or bowl 80 for containing a supply of cleaning powder indicated generally at 82. Powder bowl 80 is formed from a high-strength transparent material to permit viewing of the contents, and has its open top threaded into and supported by a rigid support housing 84. A resilient O-ring provides a fluid-tight seal between the housing and bowl. The bottom wall portion 86 of bowl 80 is tapered inwardly at an angle which will assure gravity feed of the powder mass 82 toward a central opening 88 in the bottom of the bowl. An air nozzle structure 90 is mounted on the bottom of the bowl and is connected by coupling tube 56 to line 54 to direct air under pressure upward through an elongated powder supply tube 92.

Supply tube 92 extends axially through bowl 80 and has its open bottom end in fluid communication with the opening 88. A plurality of radially spaced powder dispensing openings 94 are formed in and extend through the wall of tube 92 at its bottom end to permit a limited, metered flow of cleaning powder into the bottom portion of the tube. Air flowing into tube 92 below openings 94 entrains the cleaning powder and carries it upward through the center of the bowl to be discharged from the top end of the tube. Air turbulence in the vicinity of the openings 94 produces an erosion effect on the body of powder to assist in gravity dispensing of powder through the openings to maintain a substantially uniform concentration of cleaning powder in the stream of air discharged from the top of tube 92.

Air and entrained cleaning powder discharged from tube 92 escape from the top region of the powder chamber 58 through a radially extending outlet 96 in housing 84. Tube 62 is connected in communication with the outlet 96 to deliver the air-abrasive stream to the handpiece as described above. The air and entrained cleaning powder are discharged from the top of tube 92 in a stream which strikes an inclined surface 98 on a movable baffle member 100 which redirects the powder particles in a generally horizontal direction toward outlet 96. Baffle member 100 is rotatably mounted in a central opening of a cap or closure member 102 on the open top or housing 84. A retaining flange 104 having a position indicator or pointer 106 is mounted on the upwardly projecting end of flow control member 100. Flange 104 can be rotated to change the position of surface 98 and vary the concentration of cleaning powder contained in air discharged from outlet 96 as described in the above-mentioned concurrently filed application.

Air admitted into the top portion of the chamber from line 74 through restricter 76 and filter 78 mixes with the powder-laden air in the top portion of the powder dispenser and escapes through outlet 96. Thus, the volume of air flowing in tube 62 is greater than that admitted through tube 54 into the bottom of the powder chamber.

Figure 3:
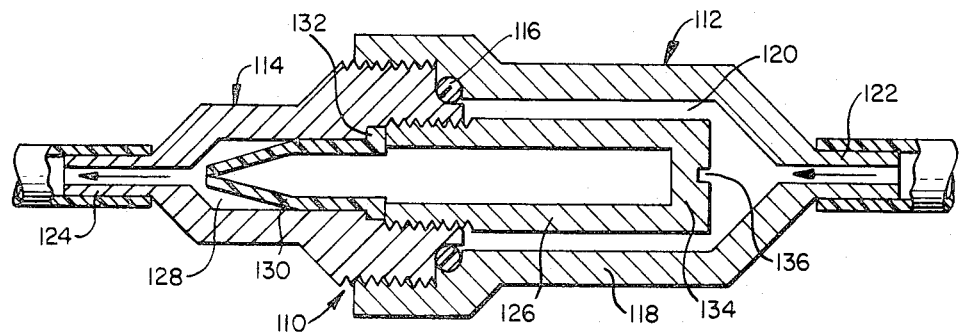
FIG. 3 is an enlarged longitudinal sectional view of the improved servicable air filter according to the invention.

Referring now to FIG. 3, the improved servicable air filter and check valve assembly of the type employed at 60 and 52 the schematic of FIG. 1 is designated generally by the reference numeral 110 and includes a hollow housing made up of housing members 112, 114 and a resilient O-ring 116 cooperates with and forms a fluid-tight seal between the two housing elements. Housing member 112 has a cylindrical body portion 118 defining an air chamber 120. A reduced diameter inlet 122 on housing member 112 is adapted to telescopingly receive a resilient flexible hose member to supply air under pressure to the chamber 120, and female threads at the opposite end of housing member 112 are adapted to threadably engage cooperating male threads on housing member 114.

Housing member 114 has a reduced diameter outlet 124 which is also adapted to receive a resilient flexible tube in fluid-tight relation, and female threads at the opposite end of member 114 are adapted to engage male threads on the open end portion of a rigid sintered metal filter element 126. The housing member 114 has a substantially cylindrical, hollow interior 128 adapted to receive a resilient "duck bill" one-way valve element 130 adapted to permit the flow of air through the element in the direction of outlet 124, but to collapse and prevent the flow of air in the reverse direction. Resilient valve element 130 is retained in the chamber 128 by a flange 132 disposed between a shoulder on the interior surface of housing member 114 and the open end of filter element 126.

The filter element 126 is in the form of an elongated tube having one end open and the other end closed by an integrally formed end wall 134. A recessed slot 136 is formed in end wall 134 for receiving a screw driver blade, coin, or the like to facilitate installation and removal. The outside diameter of the filter element 126 is less than the inside diameter of air chamber 120 so that air flowing into the housing through inlet 122 can completely surround the filter element. The filter element 126 is formed from a corrosion and tarnish resistant sintered metal material, preferably a sintered stainless steel material, which will have adequate strength to withstand installation, removal and cleaning operations. Cleaning of the filter element can be accomplished by various means such as by reverse flow of air, by washing in water or a suitable solvent, or by use of an ultrasonic cleaning and sterilizing equipment of the type frequently exployed in dental offices. Preferably housing 112 is formed from a transparent material which will permit viewing of the filter element.

Resilient valve element 130 can also easily be removed and replaced, at very low cost, so that the combined filter and one-way valve assembly may be employed over extended periods of time. The ability of the filter element to be easily serviced makes use of the entire system more reliable than with the prior art disposable filter elements. Also, the one-way valve element in the assembly prevents contamination of the filter element by reverse flow of powder containing air which right possibly occur during bleed-off of the system.

Figure 4:
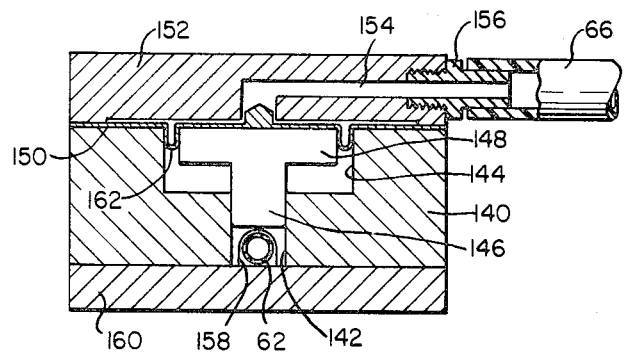
FIG. 4 is an enlarged sectional view of an improved pressure actuated pinch valve employed in the system.

As shown in FIG. 4, the pinch valve 64 includes a valve block 140 having a bore 142 extending therethrough and a counterbore 144 extending from one surface of the block 140 in coaxial relation with bore 142. A piston member 146 is slideably mounted in bore 142, with an enlarged head 148 on piston 146 being disposed in counterbore 144. A substantially disc-shaped actuating diaphragm and seal member 150 is mounted on the end of block 140 and extends over the counterbore 144, with an inlet plate 152 extending over and retaining diaphragm sealing member 150 in position. Suitable fastener means, not shown, extend through openings in inlet plate 152 and threadably engage block 140 to retain the inlet and diaphragm in position with the diaphragm engaging the adjacent end surface of enlarged head 148. An inlet bore 154 is provided in inlet plate 152 to admit air from tube 66 through a suitable fitting 156.

An arch-shaped groove 158 is formed in valve block 140 on the surface opposite the diaphragm 150, with groove 158 extending diametrically across the bore 142, and a cover plate 160 is mounted on block 140 and extends over groove 158. The groove 158 is dimensioned to receive powder delivery tube 62, with the outer surface of tube 62 engaging the end of piston 146. When air under pressure is admitted through line 66 to act on the surface of diaphragm 150, piston 146 will be moved downward with sufficient force to collapse and firmly clamp the resilient tube 62 to positively stop the flow of air and cleaning powder through the tube. Diaphragm 150 has a resilient annular ring portion indicated schematically at 162 which permits the central portion of the diaphragm to move downward against enlarged head 148 upon the application of pressure through tube 66. Upon release of pressure from the tube 66, pressure in tube 62, acting through the resilient wall of the tube, will move piston 146 and diaphragm 150 back to the position shown in FIG. 4.

The continuous diaphragm 150 seals the chamber of the piston 146 and the enlarged head 148 to prevent any contamination which might be contained in the actuating air from entering and being trapped in the chamber. This results in a longer lasting, more trouble-free operation of the valve and consequently a more positive shut-off of air and cleaning powder through tube 62 when the solenoid actuated valve 70 is actuated to direct pressure air through tube 66. Further, the enlarged area of the diaphragm subjected to the pressure enables a greater force to be applied to the piston to further assure a positive shut-off.

Referring again to FIG. 2, in accordance with the present invention the flow restricter 76 in line 74 preferably is in the form of a threaded fitting having a small diameter orifice or bore 170 extending therethrough threadably mounted in body member 84 and communicating with an inlet opening 172 leading into the chamber 58. Also, filter 78 is preferably formed from sintered stainless steel and is mounted within housing 84 in communication with the air inlet 172.

When pinch valve 64 is energized closed and valve 40 is also closed, pressure from chamber 58 will be bled off through the sintered filter 78 and flow-restricting orifice 170. This gradual bleeding of pressure from within the chamber reduces the tendency of powder particles to be drawn from the chamber. Further, since the filter 78 is mounted inside the chamber, the necessity for a separate filtered bleed line for the chamber is eliminated.

Referring again to FIG. 1, with valve 40 open to admit air under pressure to flow into line 46, and with the pinch valve 64 closed, chamber 58 will be pressurized by air flowing through lines 54 and 74, but no cleaning powder will be dispensed. Under this condition, air will flow through flow restricter 50 and filter 52 to the handpiece and be continuously bled from the head 14 at the rate determined by the position of flow restricter valve 50. Upon actuation of foot control 36 to position solenoid valve 70 to open pinch valve 64, air and cleaning powder will immediately comxence to flow through line 62 and be mixed with the air flowing through line 46 for discharging from the handpiece. During this time, air will flow through lines 54 and 74 simultaneously to provide the desired volume of cleaning powder in the air as determined by the position of baffle deflector 100.

While the preferred embodiment of the air abrasive supply system for an abrasive powder tooth cleaning apparatus has been disclosed, it is not intended that the invention be so restricted but rather it is intended to include all the embodiments which would be apparent to one skilled in the art and which come within the spirit and scope of the invention.

What is claimed is:

1. In a system for cleaning teeth in which a stream of air and entrained cleaning powder particles and a separate stream of water are directed against the tooth surface to be cleaned from a nozzle assembly in a manually controlled handpiece, the system including a fluid-tight chamber for containing a supply of cleaning powder from which the powder is discharged in an air stream from an opening in the chamber above the cleaning powder supply, said system comprising, in combination, first air conduit means for supplying air under pressure to the handpiece, second air conduit means connected to said first fluid conduit for directing a stream of air under pressure from the first air conduit means into the bottom portion of the fluid-tight chamber for entraining cleaning powder into the stream to be discharged through the outlet opening in the fluid-tight chamber, third air conduit means connected to said first fluid conduit means and to the fluid-tight chamber for directing a flow of air from the first air conduit means into the chamber at a point above the level of cleaning powder in the chamber, said third air conduit means including flow restricter means for limiting the flow of air therethrough, first air filter means connected in fluid communication with the third fluid conduit means and being located within said fluid-tight chamber for filtering air flowing into the fluid-tight chamber from the third fluid conduit means, fourth air conduit means connecting the outlet from said fluid-tight chamber to said first air conduit downstream of said second and third air conduit means whereby air and cleaning powder discharged from the outlet of the fluid-tight chamber will be mixed with the air flowing through said first air conduit means to the handpiece for delivery in a stream onto the tooth surface to be cleaned, pinch valve means in said fourth air conduit means, said pinch valve being operable to interrupt the flow of air and cleaning powder through said fourth air conduit means while permitting air to flow through said first air conduit means to the handpiece, and first and second one-way filter means connected in said first and in said second air conduit means, respectively, said one-way filter means each including check valve means operable to prevent the reverse flow of air through the filter.

2. The system defined in claim 1 further comprising a second valve means connected with said first air conduit means upstream of said second and third air conduit means, said second valve means being closable to prevent the flow of air through the system from the said first air conduit means, said first air filter means permitting the flow of filtered air from the fluid-tight chamber through said third air conduit means into said first air conduit means downstream of said second valve means to vent air pressure from the fluid-tight chamber when said second valve means and said pinch valve means are closed.

3. The system defined in claim 2 wherein said first filter means comprises a sintered metal filter element exposed to the atmosphere in the fluid-tight chamber at a location above the level of cleaning powder in the chamber.

4. The system defined in claim 2 wherein said pinch valve comprises a valve block having a bore extending therethrough and a counterbore extending inwardly into the block in coaxial relation with said bore, a piston mounted in said bore, said piston having an enlarged head positioned within said counterbore, a fluid-tight diaphragm extending over said valve block and covering said counterbore, cover plate mounted on said block in overlying relation with said diaphragm, said cover plate having an air inlet for directing air under pressure between said cover plate and said diaphragm, said diaphragm being capable of deflection by the air under pressure admitted through said inlet to engage said enlarged head and move said piston in said bore, and a flexible conduit receiving opening extending through said block and diametrically across said bore for receiving said fourth air conduit means in position to be engaged by said piston upon movement thereof in the bore by the diaphragm, said fourth air conduit means including a resilient flexible conduit extending through said conduit receiving opening whereby movement of said piston will pinch the flexible conduit and prevent flow of air and cleaning powder therethrough.

5. The invention defined in claim 4 further comprising fifth air conduit means connected with said first air conduit means for supplying air under pressure to the air inlet in said cover plate, and solenoid actuated valve means connected in said fifth air conduit means for controlling the flow of pressure air through said fifth air conduit means to said pinch valve, said solenoid actuated valve means being selectively operable to control the flow of cleaning powder and air through said fourth air conduit means.

6. The system defined in claim 5 wherein said first and second one-way filters each comprise a fluid-tight hollow housing having an inlet and an outlet and a fluid flow path extending through the housing from the inlet to the outlet, and
a sintered metal filter element removably mounted within said housing in said fluid flow path.

7. The system defined in claim 6 further comprising means for opening said housing to provide access to said sintered metal filter element, said sintered metal filter elexent being removable from said housing and being capable of being cleaned and reused.

8. The system defined in claim 7 further comprising a second valve means connected with said first air conduit means upstream of said second and third air conduit means, said second valve means being closable to prevent the flow of air through the system from the said first air conduit means, said first air filter means permitting the flow of filtered air from the fluid-tight chamber through said third air conduit means into said first air conduit means downstream of said second valve means to vent air pressure from the fluid-tight chamber when said second valve means and said pinch valve means are closed.

9. The system defined in claim 8 wherein said first filter means comprises a sintered metal filter element exposed to the atmosphere in the fluid-tight chamber at a location above the level of cleaning powder in the chamber.

10. The system defined in claim 1 wherein said first and second one-way filters each comprise a fluid-tight hollow housing having an inlet and an outlet and a fluid flow path extending through the housing from the inlet to the outlet, and
a sintered metal filter element removably mounted within said housing in said fluid flow path.

11. The system defined in claim 10 further comprising means for opening said housing to provide access to said sintered metal filter element, said sintered metal filter element being removable from said housing and being capable of being cleaned and reused.

12. The system defined in claim 11 further comprising one-way check valve means mounted in said housing between said sintered metal filter element and said outlet.

13. The system defined in claim 12 wherein said housing comprises first and second generally cup-shaped housing members each having one open end, said inlet and outlet, respectively, being formed one in the end of each said housing member opposite said open end, and cooperating thread means adjacent the open ends of each said housing member for releasably joining the housing members together to form a fluid-tight housing having said inlet and outlet in opposite ends thereof.

14. The system defined in claim 13 further comprising cooperating thread means on said sintered metal filter element and on one of said housing members for releasably mounting said sintered metal filter element in said housing.

15. The system defined in claim 14 wherein said sintered metal filter element mounted in said housing comprises an elongated substantially tubular sintered metal element having an integral wall closing one end, said thread means on the filter elexent being male threads formed on the end opposite said end wall.

16. For use in a dental cleaning system in which a stream of air having cleaning powder particles entrained therein and a separate stream of water are directed against a tooth surface to be cleaned and including a conduit system for supplying air under pressure to a manually controlled handpiece to convey and discharge the cleaning powder, an improved one-way renewable air filter comprising:
an elongated fluid-tight housing having an inlet and an outlet and an air flow path extending through the housing from the inlet to the outlet, said housing including first and second generally cup-shaped housing members each having one open end with said inlet and said outlet, respectively, being formed one in the end of each said housing member for releasably joining the housing members together to form said fluid-tight housing;
a sintered metal filter element removably mounted within said housing in said fluid flow path, said filter element capable of being cleaned and reused, said filter element comprising an elongated substantially tube member having one and closed by an integrally formed end wall and having male threads on its external surface adjacent the other end thereof, and wherein one of said housing members includes female threads adapted to engage the male threads on said filter element to releasably mount the filter element in said housing and wherein said one of said housing members including female threads further includes a shoulder formed therein; and
one-way check valve means mounted in said housing between said sintered metal filter element and said outlet, said valve means comprising a duck-bill valve having an annular flange secured between said shoulder of said one of said housing members and said other end of said sintered metal filter element for facilitating replacement of said valve means upon disengagement of said housing members and said filter element.

* * * * *